US012409120B2

United States Patent
Breakspear

(10) Patent No.: US 12,409,120 B2
(45) Date of Patent: Sep. 9, 2025

(54) PROCESS FOR PERMANENT WAVING KERATIN FIBERS

(71) Applicant: KAO GERMANY GMBH, Darmstadt (DE)

(72) Inventor: Steven Breakspear, Darmstadt (DE)

(73) Assignee: KAO GERMANY GMBH, Darmstadt (DE)

( * ) Notice: Subject to any disclaimer, the term of this patent is extended or adjusted under 35 U.S.C. 154(b) by 553 days.

(21) Appl. No.: 17/853,053

(22) Filed: Jun. 29, 2022

(65) Prior Publication Data

US 2023/0036311 A1 Feb. 2, 2023

(30) Foreign Application Priority Data

Jul. 13, 2021 (EP) ..................... 21185215

(51) Int. Cl.
| | |
|---|---|
| *A61K 8/41* | (2006.01) |
| *A45D 7/06* | (2006.01) |
| *A61K 8/19* | (2006.01) |
| *A61K 8/22* | (2006.01) |
| *A61K 8/24* | (2006.01) |
| *A61K 8/365* | (2006.01) |
| *A61Q 5/04* | (2006.01) |

(52) U.S. Cl.
CPC ................. *A61K 8/41* (2013.01); *A45D 7/06* (2013.01); *A61K 8/19* (2013.01); *A61K 8/22* (2013.01); *A61K 8/24* (2013.01); *A61K 8/365* (2013.01); *A61Q 5/04* (2013.01); *A45D 2200/25* (2013.01); *A61K 2800/48* (2013.01)

(58) Field of Classification Search
CPC ... A61K 8/41; A61K 8/19; A61K 8/22; A61K 8/24; A61K 8/365; A61K 2800/48; A61K 2800/884; A45D 7/06; A45D 2200/25; A61Q 5/04

See application file for complete search history.

(56) References Cited

U.S. PATENT DOCUMENTS

| | | | | |
|---|---|---|---|---|
| 2,990,832 A | * | 7/1961 | Mcdonough | A61K 8/24 424/70.2 |
| 3,071,515 A | | 1/1963 | Rudolf | |
| 4,263,277 A | * | 4/1981 | Tripathi | A61K 8/46 424/70.4 |
| 4,349,537 A | * | 9/1982 | Forbriger, Jr. | A61K 8/365 424/70.2 |
| 5,294,230 A | * | 3/1994 | Wu | A61Q 5/04 132/203 |
| 2002/0155081 A1 | * | 10/2002 | Coope | A61Q 5/04 424/70.5 |
| 2008/0142033 A1 | | 6/2008 | Sabbagh et al. | |

FOREIGN PATENT DOCUMENTS

| | | | |
|---|---|---|---|
| EP | 0 673 640 A1 | | 9/1995 |
| GB | 2 114 616 A | | 8/1983 |
| JP | H03153621 A | | 7/1991 |
| JP | 2002125744 A | * | 5/2002 |
| WO | 02/38114 A1 | | 5/2002 |

OTHER PUBLICATIONS

JP_2002125744_A—machine translation, Takashi et. al. "Cap for Permanent Wave" 2002. (Year: 2002).*
European Search Report dated Jan. 13, 2022, in connection with European Application No. 21185215.7.

* cited by examiner

*Primary Examiner* — Ali Soroush
*Assistant Examiner* — Rajan Pragani
(74) *Attorney, Agent, or Firm* — Norris McLaughlin, PA

(57) ABSTRACT

Compositions and processes disclosed herein permanent wave keratin fibers and/or human hair for achieving durable waves. The keratin fibers and/or human hair are treated with a reducing composition, a non-reducing and non-oxidizing composition comprising tris(hydroxymethyl)aminomethane, optionally a non-reducing and non-oxidizing acidic composition. Subsequently, the keratin fibers and/or human hair are treated with an oxidizing composition wherein after processing the reducing composition is rinsed off the keratin fibers and/or human hair.

8 Claims, No Drawings

PROCESS FOR PERMANENT WAVING KERATIN FIBERS

This application claims foreign priority benefit under 35 U.S.C. § 119 of the European Patent Application No. 21185215.7 filed Jul. 13, 2021.

The present disclosure relates to a process for permanent waving keratin fibers, especially human hair, for achieving durable waves.

The well-known and commonly used process for permanent waving keratin fibers involves reducing and oxidizing steps which are often perceived as fiber damaging and the results are very much dependent upon how the whole process is carried out. The fiber damage is especially due to the inappropriately selected, if not adjusted, processing period of the reducing composition. The hair may easily become overprocessed and appear, therefore, to have less strength, be brittle and especially not naturally feeling upon touching.

Another aspect is that the use and/or the need of heat application during processing of the reducing agent on the fibers. This is usually realized with external electrical heating devices and, especially in the Asian geography, a specially therefore designed machine so called heat perming machine is used. It is the observation of the applicant that unless the pre-reduced hair is processed with heat, almost no curls are obtained although the hair is considerably damaged. There is highly need for simplified and non-damaging processes for obtaining strong, natural feeling, homogenous permanent waving.

The EP 673 640 discloses a process for permanent waving hair wherein hair is treated with a reducing composition for a period of 20 min and, without rinsing off, an alkaline composition was applied comprising alkali carbonates and hydrogen carbonates for a period of 10 min and finally hair is applied an aqueous oxidizing composition. It has been observed that the process described therein does not deliver cosmetically acceptable hair qualities in terms of waving efficiency and especially in smoothness and softness.

Furthermore, JP-H03-153621 discloses a permanent shaping process wherein an acidic composition is mixed with an alkaline reducing agent composition and applied onto hair and after certain processing time an oxidizing composition is applied onto hair. The process does not deliver cosmetically appealing curls and hair qualities.

Similar process to the above is disclosed in US2008/0142033 wherein after treating hair with reducing composition, a composition comprising monovalent cation salt of organic acids is applied and finally hair is oxidized. This process as well have drawbacks in delivering less damage and effective curling to the hair which at the same time feels soft and smooth upon touching.

The pending non-published application of the applicant is on a process for permanent shaping hair wherein the hair is reduced and after rinsing off, an alkaline composition is applied and finally the hair is treated with an oxidizing agent. The application does not describe any other composition to be applied onto hair.

The pending non-published application of the applicant is on a process for permanent shaping hair wherein the hair is reduced and after rinsing off, an alkaline composition is applied which followed by an application of a composition comprising organic acid and finally the hair is treated with an oxidizing agent.

The above referred prior art are on the use of ammonia and other strongly smelling alkalizing agents and, therefore, during the process the smell burden is extremely high and disturbing the customer and the hairdresser carrying out the process. It is highly preferred to carry out the process without smell burden and without the use of any heating devices, which damages hair less, imparts hair strong curls and good cosmetic properties, especially in terms of elasticity, shine, healthy appearance, better combability and smoothness and softness.

The inventor of the present disclosure has unexpectedly found out that tris(hydroxymethyl)aminomethane (TRIS) may be used effectively as an alkalizing agent for curling hair in a process wherein application of an intermediate aqueous alkaline composition comprising TRIS onto reduced keratin fibers, especially human hair, after rinsing off the reducing composition, and which optionally subsequently treated with neutralizing acidic aqueous composition delivers soft and smooth hair with well-defined strong curls. The hair waved with such processes feels natural upon touching, has natural appearance with homogenous and intensive bouncy curls.

Thus, the first object of the present disclosure is a process for permanent waving keratin fibers, especially human hair, wherein,

- a—optionally, the keratin fibers, especially human hair, is washed and/or shampooed, and towel dried,
- b—an aqueous composition comprising one or more reducing agent is applied and left on the fibers for a period of 1 to 60 min,
- c—the fibers are rinsed off,
- d—the fibers are put on curlers,
- e—a non-reducing and non-oxidizing aqueous composition comprising tris(hydroxymethyl)aminomethane (TRIS) having a pH in the range of 7.5 to 12 is applied onto fibers and left on the fibers for a period 1 to 60 min,
- f—optionally the fibers are rinsed off,
- g—optionally a non-reducing and non-oxidizing aqueous composition is applied onto fibers comprising one or more organic and/or inorganic acids and having a pH in the range of 2 to 6.5 and optionally left on the hair for a period 1 to 60 min,
- h—optionally the fibers are rinsed off,
- i—an aqueous composition comprising one or more oxidizing agents, preferably hydrogen peroxide or bromate salt, is applied onto fibers and left on the fibers fora period 1 to 30 min,
- j—the fibers are optionally rinsed off, and
- k—the fibers are dried,
- wherein the curlers are taken off from fibers before or during processing in step i or after the step i prior to rinsing off and/or drying or after rinsing off (after step j).

The second object of the present disclosure is the use of a process of the present disclosure for achieving natural, intensive, homogeneous waves on keratin fibers, especially human hair.

The third object of the present disclosure is a kit for keratin fibers, especially human hair comprising the compositions used in the process above, namely an aqueous composition comprising one or more reducing agents, a non-reducing and non-oxidizing aqueous composition comprising TRIS and having a pH in the range of 7.5 to 12, optionally a non-reducing and non-oxidizing aqueous composition comprising one or more organic and/or inorganic acids and having a pH in the range of 2 to 6.5 and an aqueous composition comprising one or more oxidizing agents, preferably hydrogen peroxide or bromate salt.

In a further preferred embodiment of the present disclosure, in order to prevent fibers drying during processing, the fibers, especially human hair, are covered with e.g. foil or towel, especially during the periods the compositions comprising reducing agents, alkalizing agents and acids are left on the fibers.

In a further preferred embodiment of the present disclosure, the whole process is carried out at ambient temperature without using any heat and/or heating device. Without being bound by the theory, this should even further be beneficial to reduce hair damage and therefore contribute to healthy appearance and feeling of the fibers.

In the process of the present disclosure, an aqueous composition comprising one or more reducing agents is applied onto fibers. In principal any reducing agent of inorganic and organic ones and their mixtures are suitable for the purpose of the present disclosure. The preferred ones are inorganic and organic reducing agents.

Suitable inorganic reducing agents are sulfite and/or hydrogen sulfite salts such as sodium, potassium, ammonium and suitable organic reducing agents are thiogylcolic acid and/or its salts, cysteamine and/or its salts, thioglycerin and/or its salts, glycerin esters of thioglycolic acid and/or its salts, thiolactic acid and/or its salts, cysteine or its derivatives and/or its salts, and their mixtures. Preferred are thioglycolic acid and/or its salts, thiolactic acid and/or its salts, cysteine or its derivatives and/or its salts and sodium, potassium, ammonium sulfites and their mixtures. The most preferred are thioglycolic acid and/or its salts and sodium, potassium, ammonium sulfites, and their mixtures.

The total concentration of reducing agents in the aqueous composition of step b is in the range of 0.5 to 20%, preferably 1 to 15%, more preferably 2 to 12% and most preferably 3 to 10% by weight, calculated to the total of the aqueous composition.

The pH of the composition may be acidic or alkaline and preferably in the range of 3 to 12, more preferably 4 to 11 and most preferably it is alkaline and in the range of 7.5 to 10.5. The pH may be adjusted with the known organic and/or inorganic acids and alkalizing agents (see below).

The aqueous composition comprising one or more reducing agents is left on the hair for a period of 1 to 60 min, preferably 2 to 45 min, more preferably 5 to 30 min and most preferably 5 to 20 min at ambient temperature and without using any heat and/or heating device.

After rinsing off the fibers, the fibers are put on curlers and applied a non-reducing and non-oxidizing aqueous composition comprising TRIS and having a pH in the range of 7.5 to 12. The composition is left on the hair for a period of 1 to 60 min, preferably 2 to 45 min, more preferably 5 to 30 min and most preferably 5 to 20 min at ambient temperature and without using any heat and/or heating device.

The pH of the composition comprising TRIS is in the range of 7.5 to 12, preferably 8 to 11, more preferably 8.5 to 10.5 and most preferably 8.5 to 10. The pH may be adjusted by selecting the concentration of TRIS for achieving the required pH or alternatively may be adjusted using inorganic and/or organic acids.

The concentration of TRIS is in the range of 1 to 35%, preferably 2 to 30%, more preferably 2.5 to 25% and most preferably 3 to 20% by weight calculated to the total of the composition.

The composition may comprise other alkalizing agents to a maximum of 5% by weight of the TRIS concentration with the condition that the composition does not have smell burden.

These optional alkalizing agents may be comprised are the alkali hydroxides such as sodium hydroxide, potassium hydroxide, ammonia and its salts such as ammonium carbonate, ammonium hydrogen carbonate, ammonium carbamate, ammonium chloride, ammonium sulfate, ammonium phosphates such as ammonium dihydrogen phopshate, diammonium hydrogen phosphate, diammonium sodium phosphate, ammonium sodium hydrogen phosphate or ammonium disodium phosphate, ammonium nitrate, ammonium bromide, ammonium iodide, ammonium thiosulfate, ammonium molybdate, ammonium vanadate, ammonium sulfamate, ammonium citrate, ammonium salicylate, ammonium valerate, ammonium tartarate, ammonium benzoate, ammonium acetate, ammonium formiate and ammonium lactate, guanidine and its salts such as guanidine hydrochloride, guanidine carbonate, guanidine bicarbonate, and an alkyl or alkanol amine according to the general structure

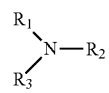

wherein $R_1$, $R_2$, and $R_3$ are same or different H, from $C_1$ to $C_4$, $C_3$ to $C_4$ unsaturated alkyl, $C_3$ to $C_4$ branched alkyl, $C_1$ to $C_4$ hydroxyl alkyl, $C_3$ to $C_4$ unsaturated hydroxyl alkyl, $C_3$ to $C_4$ branched hydroxyl alkyl, with the condition that at least one of $R_1$, $R_2$, or $R_3$ is different from H, such as monoethanolamine, diethanolamine, triethanolamine, monoethanol methylamine, monoethanoldimethylamine, diethanolmethylamine, monoethanolethylamine, monoethanoldiethylamine, diethanolethylamine, monoethanolpropylamine, monoethanoldipropylamine, diethanolpropylamine, monoethanolbutylamine, diethanolbutylamine and amino methyl propanol and their mixtures.

After an optional rinse off step, a non-reducing and non-oxidizing aqueous composition may optionally be applied onto hair comprising one or more organic and/or inorganic acids and having a pH in the range of 2 to 6.5. pH of the composition is preferably in the range of 2.5 to 5.5, more preferably 2.5 to 5 and most preferably 3 to 4.5.

The composition in step g is optionally left on the hair for a period of 1 to 60 min, preferably 2 to 45 min, more preferably 5 to 30 min and most preferably 5 to 20 min at ambient temperature and without using any heat and/or heating device.

Suitable organic acids are citric acid, succinic acid, lactic acid, malic acid, acetic acid, lactic acid, glycolic acid, tartaric acid, formic acid, oxalic acid, malonic acid, glutaric acid, adipic acid, maleic acid, fumaric acid and their salts. Preferred are citric acid, lactic acid, succinic acid, malic acid and their salts.

Suitable inorganic acids are phosphoric acid, hydrochloric acid, sulfuric acid, carbonic acid and their respective salts. Preferred are phosphoric acid and its respective salts.

The total concentration of acids is in the range of 0.1 to 20%, preferably 0.25 to 17.5% more preferably 1 to 15% and most preferably 2.5 to 15% by weight, calculated to the total of the composition.

In a further preferred embodiment of the present disclosure, in order to obtain optimal permanent shaping results and in case the hair is neutralized with an acidic composition after application of the composition comprising TRIS, the alkalinity and acidity of the aqueous non-oxidizing/non-reducing alkaline and acidic compositions are so adjusted that the 1:1, by weight, (equal amount) mixture of the two compositions has a pH in the range of 4.5 to 8, preferably 5 to 7 and more preferably 5 to 6.5.

After optional rinsing off the aqueous composition comprising one or more acids—step h of the process, an aqueous composition comprising one or more oxidizing agents, preferably hydrogen peroxide or a bromate salt is applied onto hair and left on the hair for 0.5 to 30 min, preferably 2 to 25 min, more preferably 3 to 20 min and most preferably 5 to 15 min at ambient temperature without application of any heat and/or heating device.

The fibers are preferably rinsed off at the end of the above referred processing time. Optionally the oxidizing composition may also be left on the hair, i.e. not rinsed off from hair.

The total concentration of one or more oxidizing agents, preferably hydrogen peroxide or bromate salt, in the aqueous composition is in the range of 0.1 to 15%, preferably 0.2 to 12.5%, more preferably 0.25 to 10% and most preferably 0.5 to 8% by weight, calculated to the total of the aqueous composition.

In general the pH of the oxidizing composition is in the range of 2 to 8. The pH of the composition is depending on the oxidizing agent comprised in the composition. In case of hydrogen peroxide a pH in the range of 2 to 6 is suitable. In case of sodium bromate a pH of 5 to 8 is suitable. pH of the composition may be adjusted using inorganic and/or organic acids and bases well known in the art.

The curlers are being taken off from hair prior to application of the aqueous oxidizing composition or during the period the aqueous composition is left on the hair or after rinsing off the aqueous oxidizing composition. The preferred is the curlers are taken off from hair after rinsing off the aqueous oxidizing composition.

In case that the aqueous oxidizing composition is not rinsed off from hair, the curlers may be taken off from hair either after application of the oxidizing composition or prior to application of the oxidizing composition.

In the following, all reported concentrations must be understood as relative to each of the compositions because, firstly, the compositions are not mixed with each other and secondly, the same ingredient disclosed must not be comprised in all of the compositions, although this may be possible.

Aqueous compositions, all four or one or two or three advantageously comprise a thickening agent, preferably a thickening polymer. Suitable and preferred ones are thickening polymers such as polysaccharides such as alginate, pectinate, xanthan, hydroxypropyl xanthan or dehydroxanthan, non-ionic polysaccharides such as cellulose ethers (e.g., methylcellulose, hydroxyethylcellulose (HEC), methyl hydroxyethylcellulose (MHEC), ethyl hydroxyethylcellulose (EHEC), methyl ethyl hydroxyethylcellulose (MEHEC)), starch or dextrins. Synthetic acrylate type of thickeners may as well be comprised such as acrylate copolymers and alkyl acrylates homo or copolymers also known as associative thickeners.

The concentration of the thickening polymer is very much dependent on the type of the thickening polymer and the targeted consistency (viscosity) of the compositions. Typically, the thickening polymers are comprised in the compositions at a concentration in the range of 0.1 to 3%, preferably 0.25 to 2% by weight, calculated to the total of each of the composition.

Aqueous compositions, all four or one or two or three can comprise one or more fatty alcohols. Suitable fatty alcohols are the ones with the chain length of 14 to 22 C atoms which may be saturated or unsaturated, linear or branched which may as well be substituted. Non-limiting examples are myristyl alcohol, cetyl alcohol, stearly alcohol, oleyl alcohol, behenyl alcohol, octyl dodecanol, cetostearyl alcohol, and their mixtures.

The total concentration of fatty alcohol is in the range from 0.5 to 15%, preferably 1 to 10% by weight, calculated to total of each of the composition.

Aqueous compositions, all four or one or two or three, advantageously comprise one or more surfactants. Suitable ones are selected from anionic, non-ionic, amphoteric and cationic ones.

Anionic surfactants suitable are in principle known from the cleansing compositions. These are anionic surfactants of the sulfate, sulfonate, carboxylate and alkyl phosphate type, for example, the known $C_{10}$-$C_{18}$-alkyl sulfates, and in particular the respective ether sulfates, for example, $C_{12}$-$C_{14}$-alkyl ether sulfate, lauryl ether sulfate, especially with 1 to 4 ethylene oxide groups in the molecule, monoglyceride (ether) sulfates, fatty acid amide sulfates obtained by ethoxylation and subsequent sulfatation of fatty acid alkanolamides, and the alkali salts thereof, as well as the salts of long-chain mono- and dialkyl phosphates. Preferred anionic surfactants are alkyl sulphate surfactants especially lauryl sulphate and its salts.

Further suitable surfactants are nonionic surfactants. Non-limiting examples are long-chain fatty acid mono- and dialkanolamides, such as coco fatty acid mono- or diethanolamide and myristic fatty acid mono or diethanolamide, stearic acid mono or diethanolamide, alkyl polyglucosides with an alkyl group of 8 to 18 carbon atoms, and with 1 to 5 glucoside units, sorbitan esters, such as polyethylene glycol sorbitan stearic, palmitic, myristic and lauric acid esters, fatty acid polyglycol esters or poly-condensates of ethyleneoxide and propyleneoxide, as they are on the market, for example, under the trade name "Pluronics®", as well as fatty alcohol ethoxylates, $C_{22}$-fatty alcohol ethoxylates, known by the generic terms "Laureth", "Myristeth", "Oleth", "Ceteth", "Deceth", "Steareth" and "Ceteareth" according to the CTFA nomenclature, including addition of the number of ethylene oxide molecules, e.g., "Laureth-16": The average degree of ethoxylation thereby ranges between about 2.5 and about 100, preferably about 10 and about 30.

Suitable amphoteric surfactants are in particular the various known betaines such as alkyl betaines, fatty acid amidoalkyl betaines and sulfobetaines, for example, lauryl hydroxysulfobetaine; long-chain alkyl amino acids, such as cocoaminoacetate, cocoaminopropionate and sodium cocoamphopropionate and -acetate have also been proven suitable.

Suitable cationic surfactants are according to the general structure

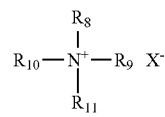

wherein $R_8$ is a saturated or unsaturated, branched or linear alkyl chain with 8-22 C atoms or

where $R_{12}$ is saturated or unsaturated, branched or linear alkyl chain with 7-21 C atoms and n has typical value of 1-4 or

where $R_{13}$ is saturated or unsaturated, branched or linear alkyl chain with 7-21 C atoms and n has typical value of 1-4, and $R_9$ is H or unsaturated or saturated, branched or linear alkyl chain with 1-22 C atoms or $R_{12}CONH(CH_2)_n$ or $R_{13}COO(CH_2)_n$ where $R_{12}$, $R_{13}$ and n are same as above.

$R_{10}$ and $R_{11}$ are H or lower alkyl chain with 1 to 4 Carbon atoms, and X is typically chloride, bromide, methosulfate.

Typical examples of those ingredients are cetyl trimethyl ammonium chloride, stearyl trimonium chloride, dipalmitoyl dimonium chloride, distearyl dimethyl ammonium chloride, stearamidopropyl trimonuim chloride, dioleoylethyl dimethyl ammonium methosulfate, dioleoylethyl hydroxyethylmonium methosulfate.

The total concentration of one or more surfactants is in the range of 0.1 to 12.5%, preferably 0.2 to 10% and more preferably 0.5-7.5% by weight, calculated to the total of each of the composition.

Further advantageously, aqueous compositions, all four, one or two or three, comprise one or more silicone compound, preferably silicone oil. Suitable and preferred ones are known with their CTFA adopted name as dimethicone and commercially available from Dow Corning under the trade name DC 200 with various viscosities.

Further advantageously, aqueous compositions, all four, one or two or three, comprise one or more cationic polymers as conditioning and/or thickening agents. Those are cationic cellulose type polymers know as Polymer JR type from Amerchol such as Polyquaternium 10 or cationic guar gum known with trade name Jaguar from Rhone-Poulenc and chemically for example Guar hydroxypropyl trimonium chloride. Furthermore, chitosan and chitin can also be included in the compositions as cationic natural polymers.

Furthermore, it has been found suitable those cationic polymers known with their CTFA category name Polyquaternium. Typical examples of those Polyquaternium 4, Polyquaternium 6, Polyquaternium 7, Polyquaternium 10, Polyquaternium 11, Polyquaternium 16, Polyquaternium 22, Polyquaternium 24, Polyquaternium 28, Polyquaternium 30, Polyquaternium 37, Polyquaternium 36, Polyquaternium 46, Polyquaternium 67, and Polyquaternium 72.

Preferred are Polyquaternium-2, Polyquaternium-6 and Polyquaternium 16. The total concentration of cationic polymers may be in the range of 0.1-2.5%, preferably 0.25-2% by weight and more preferably 0.5-1.5% by weight, calculated to total of each of the composition.

Further advantageously, aqueous compositions all four, one or two or three, comprise one or more aminated silicones which may be selected from amodimethicones and grafted aminated silicones. Suitable ones are available under various trade names such as DC 969, Belsil from Wacker Chemie AG and known with the CTFA adopted name Amodimethicone, and Elastomer OS from Kao Corporation known with CTFA adopted name Polysilicone-9.

Furthermore, aqueous compositions, all four, one or two or three, comprise one or more organic solvent which may act as penetration enhancer and/or solubilizing agent for the compounds not readily soluble in the aqueous medium. The suitable ones are 2-phenoxyethanol, benzyl alcohol, 2-phenylethanol and 2-benzyloxyethanol. Suitable aliphatic alcohols are ethanol, isopropanol, propanol, n-butanol, isobutanol, t-butanol and 1-pentanol.

Concentration of one or more organic solvent is in the range of 0.1 to 15%, preferably 0.5 to 12.5% and more preferably 1 to 10% and most preferably 1 to 7.5% by weight calculated to the total of each of the composition.

The aqueous compositions, all four, one or two or three, may advantageously comprise urea, at a concentration in the range of 0.1 to 20%, preferably 1 to 15% by weight calculated to the total of the compositions.

Additionally, the aqueous compositions, all four, one or two or three, comprise one or more polyols. Suitable ones are glycerine, phytantriol, panthenol, ethyleneglycol, polyethyleneglycols, propylene glycols such as 1,2 propylene glycol, 1,3-propylene glycol and polypropylene glycols.

The total concentration of one or more polyol is in the range of 0.1 to 15%, preferably 0.25 to 12.5%, more preferably 0.5 to 10% and most preferably 1 to 7.5% by weight calculated to the total of each of the composition.

The aqueous compositions, all four, one or two or three, can comprise one or more amino acids and/or their water soluble salts. Suitable ones are glycine, histidine, citrullin, asaparagine, alanine, valine. Leucine, isoleucine, proline, tryptophan, phenylalanine, methinone, serine, tyrosine, threonine and glutamine.

The total concentration of one or more aminoacids and/or their water soluble salts is in the range of 0.01 to 2.5%, preferably 0.1 to 2%, more preferably 0.15 to 1.5% and most preferably 0.2 to 1% by weight calculated to the total of each of the composition.

Any of the compositions described in detail above may comprise ingredients customarily found in such compositions such as preservative, fragrance, chelating agents, radical scavenger, etc.

Following examples are to illustrate the disclosure, but not to limit it.

EXAMPLE 1

The following compositions were used in carrying out the disclosure and comparing it with compositions not comprising the alkalizing agent claimed in the process of the present disclosure.

Aqueous Reducing Composition

|  | % by weight |
| --- | --- |
| Ammonium thioglycolate | 10 |
| Ammonium hydroxide | 2 |
| Phosphoric acid | q.s. to pH 8.5 |
| Water | to 100 |

Aqueous Alkaline Compositions

|  |  | % by weight | | | | | |
| --- | --- | --- | --- | --- | --- | --- | --- |
|  |  | A | B | C | D | E | F |
| Ammonium chloride |  | 2 | — | — | — | — | — |
| Ammonium hydroxide |  | 4 | — | — | — | — | — |
| TRIS |  | — | 33 | 15 | 5 | 5 | 5 |
| Sodium hydroxide | q.s. to pH | 10 | 10 | 10 | 10 | 9 | 8 |
| Water |  | q.s. to 100 | | | | | |

Aqueous Acidic Composition

|  | % by weight |
| --- | --- |
| Lactic acid | 8 |
| Sodium hydroxide | q.s. to pH 3.5 |
| Water | to 100 |

Aqueous Oxidising Composition

|  | % by weight |
| --- | --- |
| Hydrogen peroxide | 10 |
| Sodium hydroxide | q.s. to pH 3.0 |
| Water | to 100 |

A hair streak weighing approximately 5 g and having a length of 20 cm is permanently waved using the above compositions. Firstly, the streak was washed with a commercially available shampoo composition and towel dried. Afterwards, the streak was dipped into the aqueous reducing composition and left in the solution for 15 min and taken out and rinsed off with water. Afterwards, the streak was put on curlers with a diameter of 1.5 cm and dipped into the alkaline composition. After 10 min, the streak was taken out and without rinsing off, it was dipped into the aqueous acidic composition, in case the acidic treatment was carried out. After 10 min, the streak was taken out and rinsed off and dipped into the oxidizing composition for 15 min and the curlers were taken off. The streaks were rinsed off and dried. The curl ratio and observed properties of hair streaks are provided in the Table below.

The curl ratio (L) was calculated with the following equation:

$$L = ((L_0 - L_t)/L_0) \times 100$$

wherein $L_0$ is the length of the hair streak in cm prior to permanent waving, $L_t$ is the length of the hair streak in cm at the end of the permanent waving process.

The curl efficiency is not very much dependent on alkalinity of the alkaline composition comprising TRIS, similar curl ratio was observed in the pH range of 8 to 10.

More effective curling was observed in the concentration range of 5 to 15% by weight TRIS content in the alkaline composition.

EXAMPLE 2—COMPARATIVE TEST

Aqueous Reducing Composition with Tris

|  | % by weight |
| --- | --- |
| Ammonium thioglycolate | 10 |
| Ammonium hydroxide | 2 |
| TRIS | 5 |
| Phosphoric acid | q.s. to pH 8.5 |
| Water | to 100 |

Two hair streaks weighing approximately 5 g and having a length of 20 cm is permanently waved using the above compositions of Example 1. Composition E or the comparative example as above are used as the reducing compositions. One of the streaks was treated exactly in the same way as disclosed in Example 1—Streak Treated according to disclosure. The other streak—Comparative streak—washed with a commercially available shampoo composition and towel dried. Afterwards, the streak was dipped into the above aqueous reducing composition comprising TRIS and left in the solution for 15 min and taken out and rinsed off with water. Afterwards, the streak was put on curlers with a diameter of 1.5 cm and it was dipped into the aqueous acidic composition. After 10 min, the streak was taken out and rinsed off and dipped into the oxidizing composition for 15 min and the curlers were taken off. The streaks were washed and dried.

The streak treated according to the disclosure had a curl ratio of 27.4 whereas the curl ratio of the comparative streak

|  |  | A | B | C | D | E | F |
| --- | --- | --- | --- | --- | --- | --- | --- |
| Without acid treatment | Curl ratio | 4 | 10.6 | 17.6 | 20.3 | 23.3 | 21.9 |
|  | Description | Weak wave, rough feeling, damaged appearance | Strong bouncy wave, rough feeling, slightly damaged appearance | Strong bouncy curl, rough feeling, slightly damaged appearance | Intense bouncy curl, soft hand feeling, low damage appearance | Intense bouncy curl, soft hand feeling, low damage appearance | Intense bouncy curl, soft hand feeling, low damage appearance |
| With acid treatment | Curl ratio | 7.8 | 12.8 | 22.3 | 28.4 | 26.6 | 24.2 |
|  | Description | Weak wave, rough feeling, damaged appearance | Strong bouncy wave, rough feeling, slightly damaged appearance | Strong bouncy curl, soft feeling, slightly damaged appearance | Intense bouncy curl, very soft hand feeling, low damage appearance | Intense bouncy curl, very soft hand feeling, low damage appearance | Intense bouncy curl, very soft hand feeling, low damage appearance |

From the above results the following conclusions are drawn.

The alkaline treatment with TRIS comprising composition produces stronger curls and the hair treated feels soft and appears to be less damaged.

The acidic treatment after treating hair with alkaline TRIS comprising composition provides even more stronger curls and the hair treated with this process feels soft and appears to be less damaged.

was only 14.9. The streak treated with the inventive process had Intense bouncy curl, very soft hand feeling, low damage appearance whereas the comparative streak was weak wavy (lower curl ratio), rough feeling, and had clearly damaged appearance.

In a parallel comparative test, the test as above was repeated with exclusion of the acidic treatment step. Here again two parallel hair streaks were permanently shaped, the one using the same process as in Example 1 and Composition E and the other using the reducing composition as of above. The streaks were rinsed off after processing of the reducing composition, put on curlers and dipped directly into the oxidizing composition (no acidic treatment step) and after 15 min of processing, curlers were taken off and streaks were rinsed off and dried.

The streak treated according to the disclosure had a curl ratio of 27.1 whereas the curl ratio of the comparative streak was only 8.3. The streak treated with the inventive process had Intense bouncy curl, very soft hand feeling, low damage appearance whereas the comparative streak was very weak wavy (lower curl ratio), rough feeling, and had clearly damaged appearance.

These results provide clear evidence that the waving hair with the inventive process has unexpected advantageous performance over the known process from the prior art, especially WO 02/38114 A1.

The invention claimed is:

1. A process for permanently waving keratin fibers, the process comprising:
   a—washing and/or shampooing and towel drying keratin fibers;
   b—applying an aqueous composition onto the keratin fibers, wherein the aqueous compositions has a pH in the range of 3 to 12, comprises one or more reducing agents at a total concentration in the range of 0.5 to 20% by weight, calculated to a total weight of the aqueous composition in b-, and is left on the keratin fibers for a period of 1 to 60 min;
   c—rinsing off the keratin fibers;
   d—putting the keratin fibers onto one or more curlers;
   e—applying a first non-reducing and non-oxidizing aqueous composition onto the keratin fibers, wherein the first non-reducing and non-oxidizing aqueous composition comprises tris(hydroxymethyl)aminomethane (TRIS) at a total concentration in the range of 3 to 20% by weight, calculated to a total weight of the first non-reducing and non-oxidizing aqueous composition, has a pH in the range of 7.5 to 12, and is left on the keratin fibers for a period of 1 to 60 min;
   f—optionally rinsing off the keratin fibers;
   g—optionally applying a second non-reducing and non-oxidizing aqueous composition onto the keratin fibers, wherein the second non-reducing and non-oxidizing aqueous composition comprises one or more organic and/or one or more inorganic acids, has a pH in the range of 2 to 6.5, and is optionally left on the keratin fibers for a period of 1 to 60 min;
   h—rinsing off the keratin fibers;
   i—applying an aqueous composition onto the keratin fibers, wherein the aqueous composition comprises one or more oxidizing agents at a total concentration in the range of 0.1 to 10% by weight, calculated to a total weight of the aqueous composition in i—, has a pH in the range of 2 to 8, and is left on the keratin fibers for a period of 1 to 30 min;
   j—rinsing off the keratin fibers; and
   k—drying the keratin fibers,
      wherein
      the one or more curlers are taken off from keratin fibers after i—prior to rinsing of and/or drying or after rinsing off the keratin fibers after j—, and
      the process as a whole is carried out at ambient temperature without using any heat and/or heating device.

2. The process of claim 1, wherein the keratin fibers are covered with a foil or towel during the period that the aqueous compositions comprising reducing agents, tris(hydroxymethyl)aminomethane (TRIS), and acids are left on the keratin fibers.

3. The process of claim 1, wherein the one or more reducing agents are selected from sulfite and/or hydrogen sulfite salts, thiogylcolic acid and/or its salts, cysteamine and/or its salts, thioglycerin and/or its salts, glycerin esters of thioglycolic acid and/or its salts, thiolactic acid and/or its salts, cysteine and/or its salts, and at least one mixture thereof.

4. The process of claim 1, wherein the one or more organic acids are selected from citric acid, succinic acid, lactic acid, malic acid, acetic acid, lactic acid, glycolic acid, tartaric acid, formic acid, oxalic acid, malonic acid, glutaric acid, adipic acid, maleic acid, fumaric acid and their salts and one or more inorganic acids are selected from phosphoric acid, hydrochloric acid, sulfuric acid, carbonic acid, one or more their respective salts, and at least one combination thereof.

5. The process of claim 1, wherein the one or more organic and/or the one or more inorganic acids are comprised at a total concentration of in the range of 0.1 to 20% by weight, calculated to a total weight of the second non-reducing and non-oxidizing aqueous composition.

6. The process of claim 1, wherein a 1:1, by weight, mixture of the first non-reducing and non-oxidizing aqueous composition in e—and the second non-reducing and non-oxidizing aqueous composition in g—has a pH in the range of 4.5 to 8.

7. The process of claim 1, wherein one or more of the aqueous compositions of the process comprise a thickening agent, a thickening polymer and/or one or more surfactants selected from at least one anionic surfactant, at least one nonionic surfactant, at least one amphoteric surfactant, and at least one cationic surfactant.

8. The process of claim 1, wherein the total concentration of the tris(hydroxymethyl)aminomethane (TRIS) in the first non-reducing and non-oxidizing aqueous composition is in the range of 5 to 15% by weight, calculated to the total weight of the first non-reducing and non-oxidizing aqueous composition and the pH range of the first non-reducing and non-oxidizing aqueous composition is 8 to 10.

* * * * *